United States Patent
Lim et al.

(10) Patent No.: US 9,307,343 B2
(45) Date of Patent: Apr. 5, 2016

(54) METHOD OF INITIALIZING A CHANNEL IN A MEDICAL BODY AREA NETWORK

(75) Inventors: Jaewon Lim, Gyeonggi-do (KR);
Suhwook Kim, Gyeonggi-do (KR);
Bonghoe Kim, Gyeonggi-do (KR)

(73) Assignee: LG Electronics Inc., Seoul (KR)

( * ) Notice: Subject to any disclaimer, the term of this patent is extended or adjusted under 35 U.S.C. 154(b) by 148 days.

(21) Appl. No.: 14/009,162

(22) PCT Filed: Apr. 12, 2012

(86) PCT No.: PCT/KR2012/002759
§ 371 (c)(1),
(2), (4) Date: Oct. 1, 2013

(87) PCT Pub. No.: WO2012/141496
PCT Pub. Date: Oct. 18, 2012

(65) Prior Publication Data
US 2014/0024404 A1 Jan. 23, 2014

Related U.S. Application Data

(60) Provisional application No. 61/474,285, filed on Apr. 12, 2011.

(51) Int. Cl.
| | |
|---|---|
| H04B 7/00 | (2006.01) |
| H04W 4/00 | (2009.01) |
| A61B 5/00 | (2006.01) |
| H04W 48/16 | (2009.01) |
| H04L 29/08 | (2006.01) |
| H04L 29/06 | (2006.01) |
| H04W 84/18 | (2009.01) |

(52) U.S. Cl.
CPC ............. *H04W 4/005* (2013.01); *A61B 5/0024* (2013.01); *H04L 67/12* (2013.01); *H04L 69/14* (2013.01); *H04L 69/24* (2013.01); *H04L 69/28* (2013.01); *H04W 48/16* (2013.01); *H04W 84/18* (2013.01)

(58) Field of Classification Search
CPC ...... H04W 48/16; H04W 4/005; H04W 84/18
USPC ................................................ 455/41.1, 41.2
See application file for complete search history.

(56) References Cited

U.S. PATENT DOCUMENTS

| | | | | |
|---|---|---|---|---|
| 2009/0219816 A1* | 9/2009 | Rezaiifar | .......... | H04W 74/0866 370/235 |
| 2011/0176503 A1* | 7/2011 | Patel | ..................... | H04W 36/14 370/329 |

(Continued)

FOREIGN PATENT DOCUMENTS

| | | |
|---|---|---|
| KR | 10-2005-0074814 A | 7/2005 |
| WO | 2010-018518 A1 | 2/2010 |
| WO | 2010-018520 A1 | 2/2010 |

OTHER PUBLICATIONS

International Search Report issued in corresponding International Patent Application No. PCT/KR2012/002759 dated Nov. 14, 2012.

*Primary Examiner* — Wesley Kim
*Assistant Examiner* — Raj Chakraborty
(74) *Attorney, Agent, or Firm* — Morgan, Lewis & Bockius LLP

(57) ABSTRACT

According to the disclosure of the present invention, a method of a Network Body Area Network (MBAN) master to control the channel defaulting of an MBAN terminal in an MBAN system is provided. The method includes: performing an association process with the MBAN terminal through a channel of a first frequency band; and transmitting control information for the channel initialization of the MBAN terminal to the MBAN terminal. The control information includes a channel defaulting timer, and a value of the channel defaulting timer indicates a time between the timing when the MBAN terminal cannot receive a signal from a channel of the first frequency band in use and the timing when the channel search of a second frequency band starts.

11 Claims, 11 Drawing Sheets

(56) References Cited

U.S. PATENT DOCUMENTS

2011/0182222 A1* 7/2011 Patel ................... H04W 76/046
                                                                 370/311

2013/0033749 A1* 2/2013 Cheng ................ G02B 27/2264
                                                                 359/464

2013/0337749 A1* 12/2013 Wang ..................... H04W 4/008
                                                                 455/41.2

\* cited by examiner (a)            (b)

FIG. 4

| Frame Control | Sequence Number | Addressing Fields | Auxiliary Security header | SuperFrame Specification | GTS fields | Pending address fields | Beacon Payload | FCS |

FIG. 9A

| Timer t$_1$ value | Action code |
|---|---|

FIG. 9B

| Frame Control | Sequence Number | Addressing Fields | Auxiliary Security header | Timer $t_1$ value | Action code | Frame Payload | FCS |
|---|---|---|---|---|---|---|---|

METHOD OF INITIALIZING A CHANNEL IN A MEDICAL BODY AREA NETWORK

This is a U.S. National Phase Entry of PCT Application No. PCT/KR2012/002759 filed Apr. 12, 2012, and claims the benefit of U.S. Provisional Application No. 61/474,285 filed Apr. 12, 2011.

TECHNICAL FIELD

The present invention relates to a channel switching method and apparatus, and more specifically, to a method and apparatus for a terminal to initialize an operation channel in a medical body area network.

BACKGROUND ART

The medical body area network (MBAN) system has been devised to provide a flexible platform for wireless networking of multiple sensors used for monitoring a patient's physiological data in a healthcare facility, such as a hospital.

The MBAN system operates in a band of 2360 MHz to 240 MHz based on IEEE 802.15.4 and its maximum emission bandwidth is restricted to 5 MHz.

The transmission power of the MBAN system, when operating in 2360 to 2390 MHz, has the smaller one of 1 mW and 10*log (B) dBm. At this time, B is 20 dB emission bandwidth. When operating in 230 to 2400 MHz, the MBAN system uses the smaller value of 20 mW and 10*log (B) dBm as its transmission power. At this time, B is 20 dB emission bandwidth.

2360 to 2400 MHz is a frequency band allocated for another wireless communication system, and the MBAN system operates based on wireless recognition technology. This wireless recognition technology refers to a communication technology in which a network or wireless communication apparatus actively senses and determines the ambient communication environment to adaptively vary transmission/reception characteristics, such as frequency band, transmission power, and encoding scheme, for the optimal communication. At this time, the wireless recognition apparatus, upon sensing the use of other licensed users or primary users in the frequency band the device intends to use, is operated not to interfere with the communication of the other users, among others.

For such purpose, in the MBAN, in the case of operation in a band of 2360 to 2390 MHz, MBAN apparatuses operate in a registered healthcare facility, in principle. In other words, the use of 2360 to 230 MHz should be controlled in cooperation with other licensed users, and when the other licensed users use the corresponding band, all the operations should be initialized in this band, and the operations should be resumed by newly using a band of 2390 to 2400 MHz.

When the MBAN apparatuses move to the outside, their operation should be stopped or their transmission band needs to be changed to a band of 2390 to 2400 MHz that is used as a basic band before transmission. When operating in 2390 to 2400 MHz, the MBAN apparatuses may be used without a limitation on whether it is located indoors or outdoors.

In the conventional MBAN system, when a specific instant occurs, a method is not specifically defined by which the MBAN terminal initializes a channel of a band of 2360 to 2390 MHz and switches to a band of 2390 to 2400 MHz.

DETAILED DESCRIPTION OF INVENTION

Technical Problems

Accordingly, this disclosure aims to suggest a channel initializing method for an MBAN. Further, an object of this disclosure is to provide an apparatus of performing the method.

Technical Solutions

To achieve the above objects of the present invention, according to an embodiment of the present invention, a method of an MBAN (Medical Body Area Network) master to perform channel initialization on an MBAN terminal in an MBAN system is provided. The method comprises performing an association process with the MBAN terminal through a channel of a first frequency band; and transmitting control information for channel initialization of the MBAN terminal to the MBAN terminal, wherein the control information may include a channel initializing timer, and wherein a value of the channel initializing timer indicates a period from a time when the MBAN terminal cannot receive a signal through a channel of the first frequency band being used to a time when the MBAN terminal starts to search a channel of a second frequency band.

The control information may be determined by an MBAN controller. The control information may be determined by the MBAN master.

The control information may be determined based on one or more of the type of a service being used by the MBAN terminal, a history of access of the MBAN terminal to a channel, or an operation scheme of the MBAN master.

Transmitting the control information to the MBAN terminal may include transmitting the control information in a unicast scheme.

The control information may further include an action code, and wherein the action code indicates searching the channel of the second frequency band after searching other channels of the first frequency band.

The control information may further include an action code, and wherein the action code indicates searching the channel of the second frequency band without searching other channels of the first frequency band.

The first frequency band may be a band of 2360 MHz to 2390 MHz, and the second frequency band may be a band of 2390 MHz to 2400 MHz.

According to another embodiment of the present invention, a method of an MBAN (Medical Body Area Network) terminal to initialize an operation channel in an MBAN system is provided. The method comprises receiving control information for channel initialization of the MBAN terminal from an MBAN master, wherein the control information may include a channel initializing timer; and initializing an operation in a first frequency band when failing to receive a signal through a channel of the first frequency band for a time set by the channel initializing timer; and starting to search a channel of a second frequency band.

The first frequency band may be a band of 2360 MHz to 2390 MHz, and the second frequency band may be a band of 2390 MHz to 2400 MHz.

Starting to search the channel of the second frequency band may include searching the channel of the second frequency band after searching other channels of the first frequency band.

Starting to search the channel of the second frequency band may include searching the channel of the second frequency band without searching other channels of the first frequency band.

According to still another embodiment of the present invention, an MBAN master is provided. The MBAN master comprises a controller controlling channel initialization of an MBAN (Medical Body Area Network) terminal; and a wireless communication unit communicating with the MBAN terminal under the control of the controller, wherein the controller performs an association process with the MBAN terminal through a channel of a first frequency band and controls the wireless communication unit to transmit control information for channel initialization of the MBAN terminal to the MBAN terminal, wherein the control information may include a channel initializing timer, and wherein a value of the channel initializing timer indicates a period from a time when the MBAN terminal cannot receive a signal through a channel of the first frequency band being used to a time when the MBAN terminal starts to search a channel of a second frequency band.

The control information may be determined by an MBAN controller, and wherein the determination may be made based on one or more of the type of a service being used by the MBAN terminal, a history of access of the MBAN terminal to a channel, or an operation scheme of the MBAN master.

The control information may be determined by the MBAN master, and wherein the determination may be made based on one or more of the type of a service being used by the MBAN terminal, a history of access of the MBAN terminal to a channel, or an operation scheme of the MBAN master.

The control information may further include an action code, and wherein the action code indicates searching the channel of the second frequency band after searching other channels of the first frequency band, or the action code indicates searching the channel of the second frequency band without searching other channels of the first frequency band.

The first frequency band may be a band of 2360 MHz to 2390 MHz, and the second frequency band may be a band of 2390 MHz to 2400 MHz.

According to yet still another embodiment of the present invention, an MBAN terminal is provided. The MBAN terminal comprises a controller controlling channel initialization; and a wireless communication unit communicating with an MBAN master under the control of the controller, wherein the controller performs an association process with the MBAN master through a channel of a first frequency band, receives control information for channel initialization of the MBAN terminal, wherein the control information may include a channel initializing timer, and when failing to receive a signal through a channel of the first frequency band for a time set by the channel initializing timer, controls the wireless communication unit to initialize an operation in the first frequency band and to start to search a channel of a second frequency band.

The control information may further include an action code, and wherein the controller may control the wireless communication unit to, according to the action code, search the channel of the second frequency band after searching other channels of the first frequency band, or search the channel of the second frequency band without searching other channels of the first frequency band.

Advantageous Effects

According to an embodiment of the present invention, the MBAN terminal may perform channel initialization more efficiently. Accordingly, the MBAN terminal and an MBAN master may communicate with each other more stably.

BRIEF DESCRIPTION OF DRAWINGS

FIG. 4 is a view illustrating a structure of a beacon frame used in an IEEE 802.15.4 system.

FIGS. 9a and 9b are views each illustrating a frame including control information for channel initializing an MBAN terminal according to embodiments of the present invention.

BEST MODE

Figure 1:
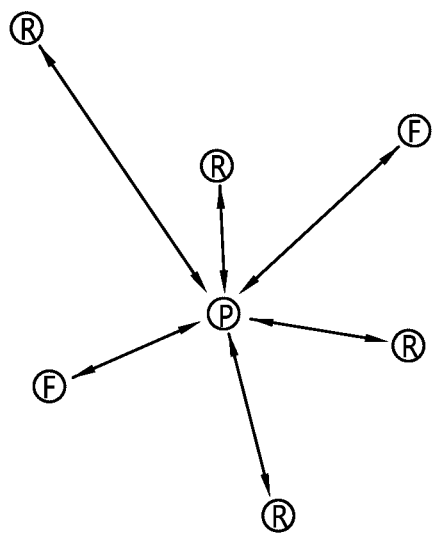
FIG. 1 illustrates an example of an IEEE 802.15.4-based network topology.
Figure 1:
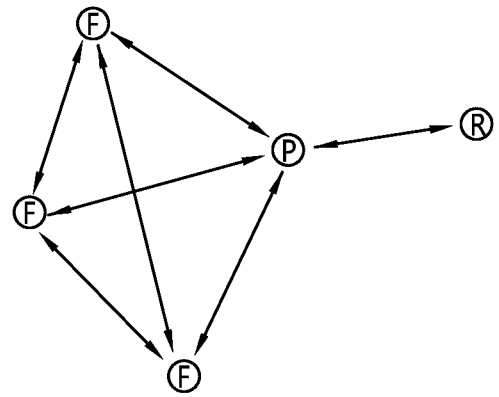

As used herein, the technical terms are used merely to describe predetermined embodiments and should not be construed as limited thereto. Further, as used herein, the technical terms, unless defined otherwise, should be interpreted as generally understood by those of ordinary skill in the art and should not be construed to be unduly broad or narrow. Further, when not correctly expressing the spirit of the present invention, the technical terms as used herein should be understood as ones that may be correctly understood by those of ordinary skill in the art. Further, the general terms as used herein should be interpreted as defined in the dictionary or in the context and should not be interpreted as unduly narrow.

As used herein, the singular form, unless stated otherwise, also includes the plural form. As used herein, the terms "including" or "comprising" should not be interpreted as necessarily including all of the several components or steps as set forth herein and should rather be interpreted as being able to further include additional components or steps.

Further, as used herein, the suffixes "module" or "unit" as used for components are mixed up for ease of drafting this disclosure and do not have separate or distinguished meanings or functions from each other.

Further, as used herein, the terms "first" and "second" may be used to describe various components, but these components are not limited thereto. The terms are used only for distinguishing one component from another. For example, without departing from the scope of the present invention, a first component may also be referred to as a second component, and the second component may likewise be referred to as the first component.

Hereinafter, preferred embodiments of the present invention will be described in detail with reference to the accompanying drawings. The same reference numerals may refer to the same or similar elements throughout the specification and the drawings.

When determined to make the gist of the present invention unclear, the detailed description of the present invention is skipped. Further, the accompanying drawings are provided merely to give a better understanding of the spirit of the present invention, and the present invention should not be limited thereto.

FIG. 1 illustrates an example of an IEEE 802.15.4-based network topology.

Two types of devices, such as an FFD (Full Function Device) and an RFD (Reduced Function Device), may participate in the IEEE 802.15.4 network. The FFD performs functions such as initialization of the network, node management, or storing node information. An FFD that allows the other devices to configure a network is referred to as a "PAN (Personal Area Network) coordinator."

The FFD is a device that may perform a coordinator function, and this device may configure various types of network topologies. The FFD may communicate with an FFD and the RFD both. The FFD consumes relatively much power to perform the coordinator function and thus is usually wiredly powered.

In contrast, the RFD is a device that cannot perform the coordinator function and is a target that is to be coordinated by the FFD. In other words, the RFD communicates with only the FFD and the FFD is fully in charge of networking functions. Accordingly, a minimum size of stack structure may be used, and computation/memory resources may be saved. Therefore, right after discovering a PAN coordinator and transmitting data to it, the RFD may disconnect itself therefrom and enter into a saving (sleep) mode, resulting in much less power consumption and prolonged battery use.

In FIG. 1, "F" denotes the FFD, "R" denotes the RFD, and "P" denotes the PAN coordinator.

FIG. 1 illustrates two types of network topologies that may be created by the IEEE 802.15.4 system. (a) of FIG. 1 illustrates an example of a star network, and (b) of FIG. 1 illustrates an example of a peer-to-peer network.

In the star topology, communication is performed only between the devices and the PAN coordinator. At this time, the devices are start and end points of the communication, while the PAN coordinator may be a start point, an end point, or a router.

In the peer-to-peer topology, each device may communicate with any of the other devices in the network. Accordingly, a more complicated network may be configured such as a mesh network.

The star network may operate devices so that their battery life lasts long. The peer-to-peer network may configure one or more data delivery paths, thus providing for high data reliability and access recognition rate.

Figure 2:
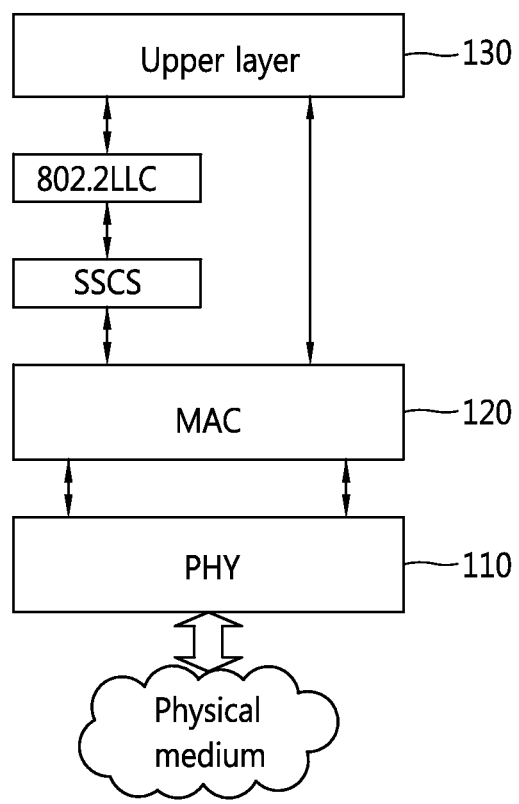
FIG. 2 illustrates a protocol stack structure in an IEEE 802.15.4 system.

FIG. 2 illustrates a protocol stack structure in an IEEE 802.15.4 system.

As can be seen from FIG. 2, the IEEE 802.15.4 protocol stack consists of a PHY (physical) layer 110, an MAC (Medium Access Control) layer 120, and an upper layer 130.

The PHY layer 110 includes an RF transceiver and its related control mechanism. The PHY layer 110 may provide a PHY management service for managing the PHY layer and a PHY data service for transmitting and receiving PHY PDUs (Protocol Data Units) through the physical channel.

The MAC layer 120 provides access to a physical channel for data transmission. The MAC layer 120 may provide an MAC data service for transmitting and receiving MAC PDUs (Protocol Data Units) through the physical layer and an MAC management service for managing the MAC layer. The MAC layer 120 may perform functions such as beacon management, channel access, GTS management, frame verification, and security functions.

The upper layer 130 consists of a network layer and an application layer. The network layer provides functions, such as configuration, processing, or message routing of the network. The application layer provides a function the device aims for. By way of example, the IEEE 802.15.4 device 100 may function as an RFD (Reduced Function Device), FFD (Full Function Device), or coordinator depending on the type of a program mounted therein, that is, depending on the type of a program for processing the data of the application layer.

Figure 3:
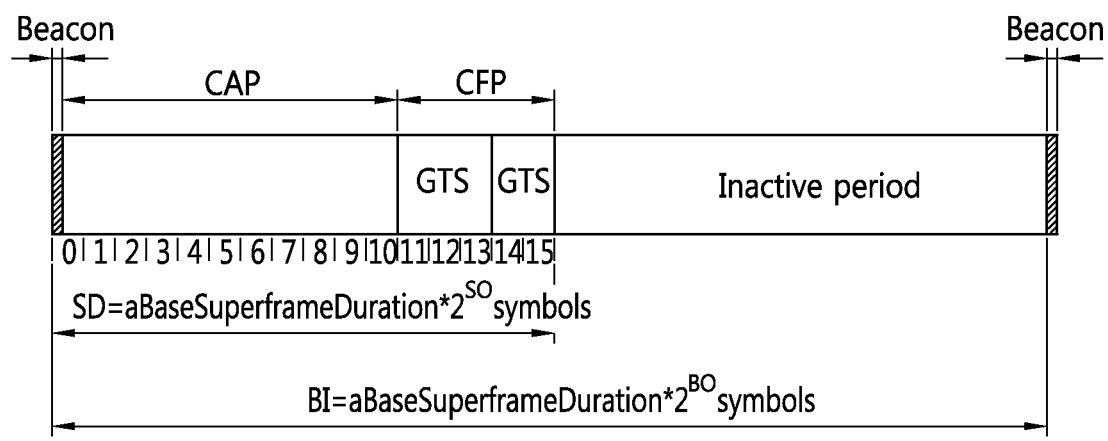
FIG. 3 is a view illustrating a structure of a super frame used in an IEEE 802.15.4 system.

FIG. 3 is a view illustrating a structure of a super frame used in an IEEE 802.15.4 system.

The IEEE 802.15.4 system includes a communication period (active period) and an inactive period depending on low-power requirements. The repetition cycle of the active period and the inactive period is referred to as "duty cycle."

The active period includes a beacon, a CAP (Contention Access Period), and a CFP (Contention Free Period) and data transmission primarily occurs in the CAP.

The CFP includes GTSs (Guaranteed Time Slots) and each GTS may be assigned to a specific device so that the GTS may be used for the device to transmit and receive data with a PAN coordinator. Up to seven GTSs may be supported in one PAN.

What is allocated for each GTS is configured in the form of a GTS descriptor by the PAN coordinator. The GTS descriptors are included in the GTS field of the beacon and are transmitted by the PAN coordinator.

FIG. 4 is a view illustrating a structure of a beacon frame used in an IEEE 802.15.4 system.

Each field of the beacon frame follows what is defined in IEEE 802.15.4.

In particular, what is allocated for each GTS is configured by the PAN coordinator in the form of a GTS descriptor. The GTS descriptors are included in the GTS field of the beacon and are transmitted by the PAN coordinator.

Figure 5:
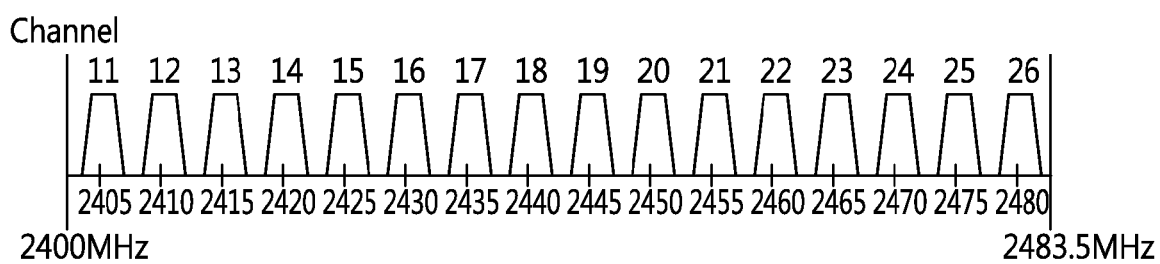
FIG. 5 is a view illustrating a channel arrangement of an IEEE 802.15.4 system.

FIG. 5 is a view illustrating a channel arrangement of an IEEE 802.15.4 system.

As can be seen in FIG. 5, the IEEE 802.15.4 system operating in a band of 2400 MHz has a channel spacing of 5 MHz.

An MBAN system based on the IEEE 802.15.4 system uses a band of 2360 to 2390 MHz and a band of 2390 to 2400 MHz. The band of 2360 to 2390 MHz may be used when the MBAN terminal in the healthcare facility is allocated with a channel from the MBAN master and operates (hereinafter, "MBAN PAN coordinator," "PAN coordinator," and "MBAN coordinator" have the same meaning). The band of 2390 to 2400 MHz is used when the MBAN terminal cannot receive information on the MBAN channel from the MBAN coordinator any longer or when the MBAN terminal and the coordinator operate outside the healthcare facility. Further, the band of 2390 to 2400 MHz may also be used as a basic channel band of the MBAN system.

Figure 6:
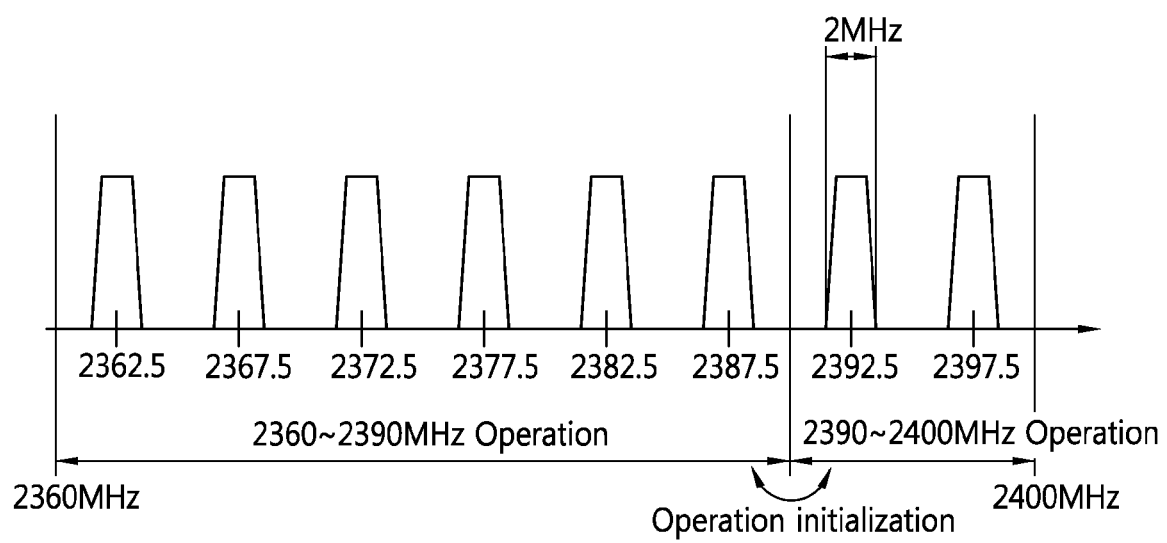
FIG. 6 is a view illustrating an example of a channel arrangement in a medical body area network.

FIG. 6 illustrates an example of a channel arrangement of an MBAN system.

In FIG. 6, available channels of the MBAN in a band of 2360 to 2400 MHz are marked. The MBAN terminal operating in the band need sometimes switch its operation channel from a channel of a band of 2360 to 2390 MHz to a channel of a band of 2390 to 2400 MHz. For example, in case the MBAN terminal operates outside an area designated to be able to use the frequency band of 2390 to 2400 MHz, for example, when the MBAN terminal operates outside the healthcare facility, the MBAN terminal should switch its operation channel to a channel of a band of 2390 to 2400 MHz. Or, when failing to receive frequency selection information of the band of 2360 to 2390 MHz from the MBAN master, the MBAN terminal should switch its operation channel to a channel of the band of 2390 to 2400 MHz. In the above case, the MBAN terminal performs operation initialization (operation defaulting) and then switches the channels. At this time, the MBAN terminal, when failing to receive a response from the MBAN master for a predetermined time, initializes the operation and channel in the band of 2360 to 2390 MHz and attempts to access the MBAN master of the band of 2390 to 2400 MHz.

A channel initializing method between a band of 2360 to 2390 MHz and a band of 2390 to 2400 MHz is now described.

Figure 7:
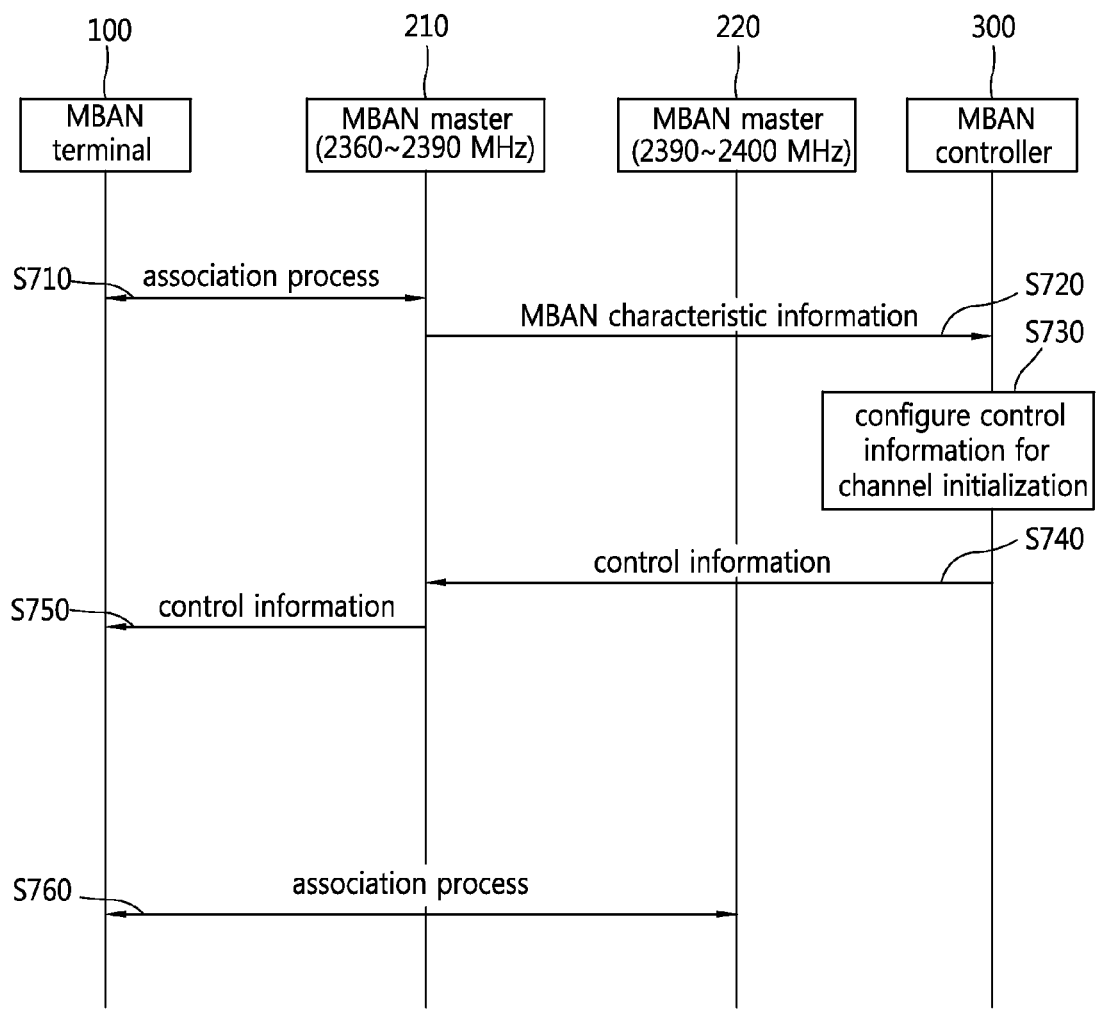
FIG. 7 is a flowchart illustrating a channel initializing method according to a first embodiment of the present invention.

FIG. 7 is a flowchart illustrating a channel initializing method according to a first embodiment of the present invention.

The MBAN system may include an MBAN controller, an MBAN master, and a MBAN terminal. The MBAN controller may include a database (DB) for storing and managing a channel status of each frequency band, a MBAN coordinator for managing the DB, and a MBAN control point. A plurality of MBAN control points may be present under one MBAN coordinator, and each MBAN control point may control one or more MBAN masters. The MBAN control point may be functionally implemented in the MBAN coordinator or may be implemented in separate hardware or software physically separated from the MBAN coordinator.

The MBAN master 210 and the MBAN terminal 100 may communicate with each other using one of channels of a band of 2360 to 2390 MHz (hereinafter, first frequency band). For this, the MBAN master 210 and the MBAN terminal 100 first perform an association process (S710). The association process is a service used for configuring a membership for a device (terminal) in the MBAN and is performed according to the procedure defined in IEEE 802.15.4. Thereafter, the MBAN master 210 may transmit characteristic information related to the MBAN terminal 100, a corresponding service or MBAN master to the MBAN controller 300 (S720). Here, the characteristic information may include the type of a service to be used by the MBAN terminal, a previous history of access of the MBAN terminal to the channel or operating scheme of the MBAN master.

The MBAN controller 300 may configure control information for channel initializing the MBAN terminal based on the received characteristic information (S730). The control information includes a channel initializing timer. The channel initializing timer may indicate the period from the time when the MBAN terminal cannot receive a signal through the channel of the first frequency band to the time when the MBAN terminal initializes the operation in the first frequency band and starts to operate in the band of 2360 to 2390 MHz (hereinafter, second frequency band). As described above, the first frequency band and the second frequency band may be separated from each other depending on whether the MBAN terminal may first use the MBAN system. That is, the first frequency band is a frequency band in which the MBAN terminal operates on a secondary basis, and the second frequency band is a frequency band in which the MBAN terminal may operate on a primary basis.

Further, the control information may include an indicator for indicating a scheme in which the MBAN terminal searches a channel of the second frequency band. The indicator may be an action code, and the action code may be one indicating searching a channel of the second frequency band after searching other channels of the first frequency band or may be one indicating searching a channel of the second frequency band without searching other channels of the first frequency band.

When receiving the control information from the MBAN controller 300, the MBAN master 210 transmits the control information to the MBAN terminal 100 (S740). At this time, the MBAN master 210 may transmit the control information in a unicast scheme, and the structure of a command frame therefor is described below with reference to FIG. 9.

When receiving the control information from the MBAN master 210, if failing to receive a signal through the channel being used in the first frequency band for the time set by the channel initializing timer included in the control information, the MBAN terminal 100 initializes the operation in the first frequency band and starts the operation in the second frequency band. At this time, if having received the action code, the MBAN terminal 100 may search a channel of the second frequency band in the way indicated by the action code. When searching a channel through which communication is possible in the second frequency band, the MBAN terminal 100 performs an association process with a master 220 having the second frequency band (S760) and then may perform transmission/reception of data.

Figure 8:
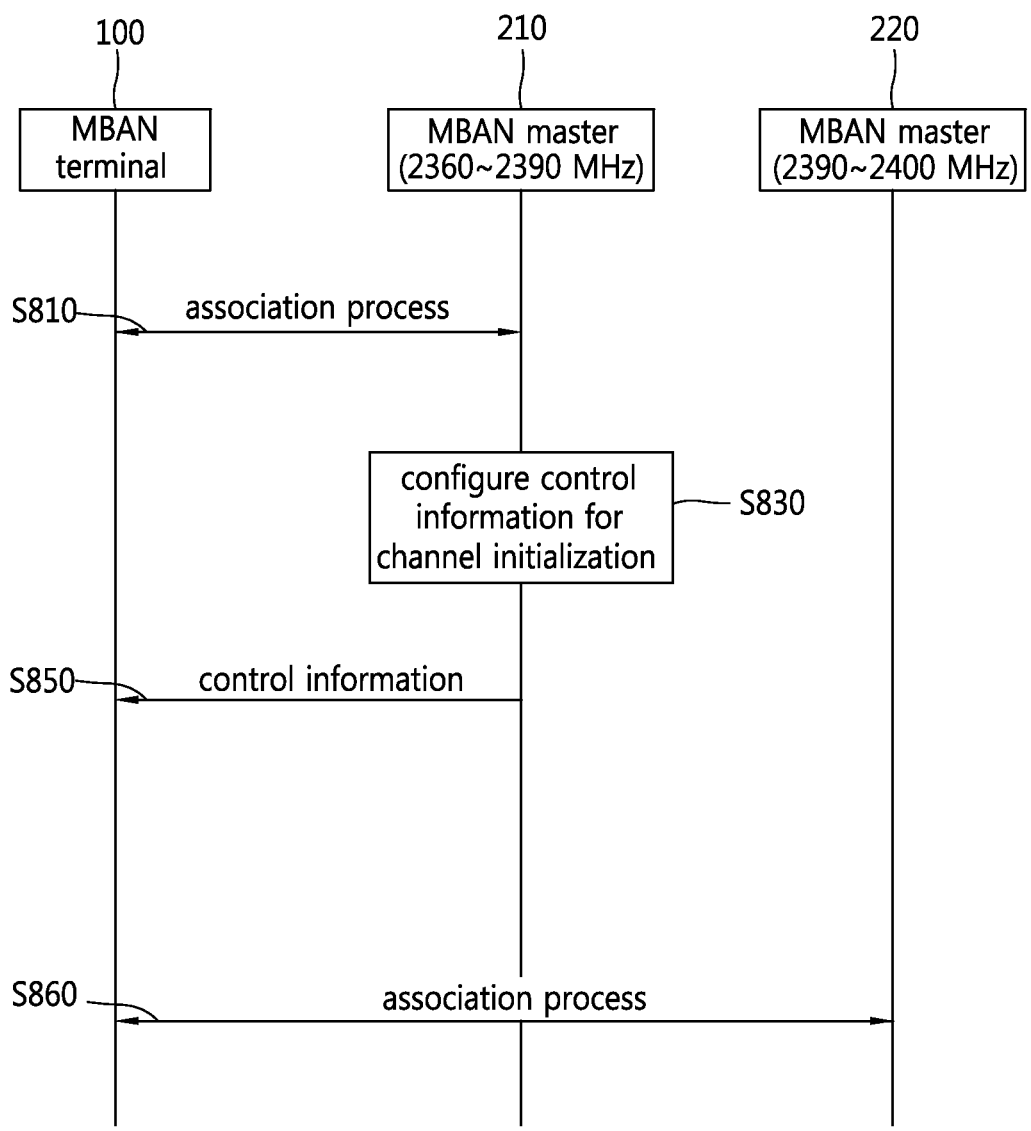
FIG. 8 is a flowchart illustrating a channel initializing method according to a second embodiment of the present invention.

FIG. 8 is a flowchart illustrating a channel initializing method according to a second embodiment of the present invention.

The MBAN master 210 and the MBAN terminal 100 may communicate with each other using one of channels of a band of 2360 to 2390 MHz (hereinafter, first frequency band). For this, the MBAN master 210 and the MBAN terminal 100 first perform an association process (S810). Unlike FIG. 7, the MBAN master 210 may configure control information for channel initializing the MBAN terminal based on characteristic information related to the MBAN terminal 100, a corresponding service or the MBAN master (S830). Here, the characteristic information may include the type of a service to be used by the MBAN terminal, a previous history of access of the MBAN terminal to the channel, or an operation scheme of the MBAN master.

The control information includes a channel initializing timer. The channel initializing timer may indicate the period from the time when the MBAN terminal cannot receive a signal through the channel of the first frequency band to the time when the MBAN terminal initializes the operation in the first frequency band and starts the operation in the band of 2360 to 2390 MHz (hereinafter, second frequency band). As described above, the first frequency band and the second frequency band are separated from each other depending on whether the MBAN terminal may first use the MBAN system. That is, the first frequency band is a frequency band in which the MBAN terminal operates on a secondary basis, and the second frequency band is a frequency band in which the MBAN terminal may operate on a primary basis.

Further, the control information may include an indicator for indicating a scheme in which the MBAN terminal searches a channel of the second frequency band. The indicator may be an action code, and the action code may be one indicating searching a channel of the second frequency band after searching other channels of the first frequency band or may be one indicating searching a channel of the second frequency band without searching other channels of the first frequency band.

When configuring the control information, the MBAN master 210 transmits the control information to the MBAN terminal 100 (S850). At this time, the MBAN master 210 may transmit the control information in a unicast scheme, and the structure of a command frame therefor is described below in detail with reference to FIG. 9.

When receiving the control information from the MBAN master 210, the operation of the MBAN terminal 100 is the same as what is described above in connection with FIG. 7.

Figure 9A:
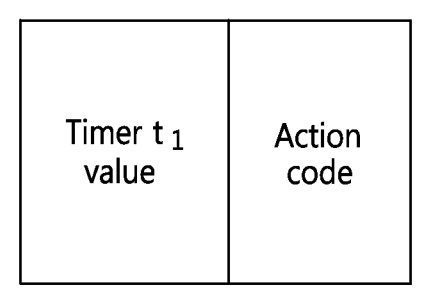

FIGS. 9a and 9b are views each illustrating a frame including control information for channel initializing an MBAN terminal according to embodiments of the present invention.

The control information may include a channel initializing timer and an action code.

FIG. 9a shows an example of control information for channel initialization.

In FIG. 9a, the timer t1 field denotes a period during which the MBAN terminal waits before performing channel initialization. That is, it denotes a period from the time when the MBAN terminal cannot receive a signal through the channel being used in the band of 2360 to 2390 MHz (hereinafter, first frequency band) to the time when the MBAN terminal initializes the operation in the first frequency band and starts the channel searching in the band of 2360 to 2390 MHz (hereinafter, second frequency band).

The action code field indicates a scheme for searching a channel of the second frequency band. That is, the action code may indicate searching the channel of the second frequency band after searching other channels of the first frequency band or may indicate searching the channel of the second frequency band without searching other channels of the first frequency band.

FIG. 9b shows an example of a command including control information for channel initialization.

When the MBAN master 200 transmits the control information to the MBAN terminal 100, a unicast scheme may be used. The unicast scheme may be performed by defining a separate command and frame for channel initialization. FIG. 9b illustrates an example of a command for such channel initialization, which may include a timer t1 value field and an action code field. When receiving the channel initializing command including the fields, the MBAN terminal may perform channel initialization as described above in connection with FIGS. 7 and 8.

Figure 10:
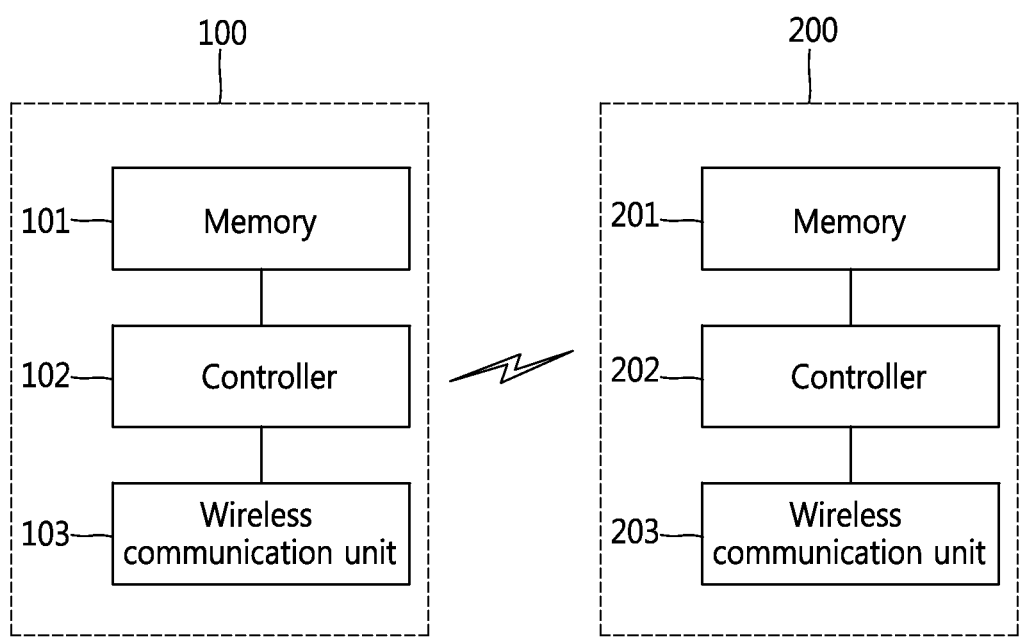
FIG. 10 is a block diagram illustrating an MBAN terminal and an MBAN master according to an embodiment of the present invention.

FIG. 10 is a block diagram illustrating an MBAN terminal and an MBAN master according to an embodiment of the present invention.

The MBAN terminal 100 may include a memory 101, a controller 102, and a wireless communication unit 103.

The memory 101 may store the methods suggested herein. Further, the memory 101 may store information related to channel initialization under the control of the controller 102. Further, the memory 101 may store information on a channel belonging to each frequency band of the MBAN.

The controller 102 controls the overall operation of the MBAN terminal and controls the memory 101 and the wireless communication unit 103. Further, the controller 102 may receive control information for channel initialization from the MBAN master. At this time, the control information may include a channel initializing timer and an action code.

The controller 102 may control the channel initialization based on the received control information.

The wireless communication unit 103 may search a channel of the MBAN system and initialize an operation channel under the control of the controller 102. At this time, the wireless communication unit 103 may search a channel of a band of 2390 to 2400 MHz after searching other channels of a band of 2360 to 2390 MHz or may search a channel of a band of 2390 to 2400 MHz without searching other channels of a band of 2360 to 2390 MHz.

The MBAN master 200 may include a memory 201, a controller 202, and a wireless communication unit 203.

The memory 201 may store the methods suggested herein. Further, the memory 201 may store information related to use of channels of MBAN frequency bands under the control of the controller 202. That is, the memory 201 may store information related to a status in which each channel is used and available time. Further, the memory 201 may store information related to channel initialization of a specific MBAN terminal.

The controller 202 controls the overall operation of the MBAN master 200 and controls the memory 201 and the wireless communication unit 203. The controller 202 may receive control information for channel initializing the MBAN terminal from the MBAN controller. Or, the control information may be determined by the controller 202 based on the type of a service being used by the MBAN terminal, a history of access of the MBAN terminal to the channel, and an operation scheme of the MBAN master. The controller 202 may transmit the information related to the channel initialization to the MBAN terminal. At this time, the information related to the channel initialization may include a channel initializing timer and an action code.

The controller 202 may transmit the information related to the channel initialization in a unicast scheme.

The wireless communication unit 203 may communicate with the MBAN terminal through a channel designated under the control of the controller 202. Or, the wireless communication unit 203 may transmit beacon and command frames to the physical channel under the control of the controller 202.

The various embodiments set forth herein may be implemented in a recording medium that may be read by a computer or a similar device using software, hardware, or a combination thereof.

Although embodiments of the present invention have been described, it will be understood by those of ordinary skill that various changes and modifications can be made thereto without departing from the scope of the present invention defined by the appended claims.

The invention claimed:

1. A method of an MBAN (Medical Body Area Network) master to perform channel initialization on an MBAN terminal in an MBAN system, the method comprising:
    performing an association process with the MBAN terminal through a channel of a first frequency band; and
    transmitting control information for channel initialization of the MBAN terminal to the MBAN terminal,
    wherein the control information includes a channel initializing timer,
    wherein a value of the channel initializing timer indicates a period from a time when the MBAN terminal cannot receive a signal through a channel of the first frequency band being used to a time when the MBAN terminal starts to search a channel of a second frequency band or another channel of the first frequency band,
    wherein the control information further includes an action code,
    wherein the action code indicates a first searching scheme or a second searching scheme,
    wherein the first searching scheme is searching the channel of the second frequency band after searching the another channel of the first frequency band,
    wherein the second searching scheme is searching the channel of the second frequency band without searching the another channel of the first frequency band,
    wherein the first frequency band is a secondary channel for the MBAN terminal,
    wherein the second frequency band is a primary channel for the MBAN terminal, and wherein the period is determined based on a type of a service being used by the MBAN terminal, a history of access of the MBAN terminal to a channel, and an operating scheme of the MBAN master.

2. The method of claim 1, wherein the control information is determined by an MBAN controller.

3. The method of claim 1, wherein the control information is determined by the MBAN master.

4. The method of claim 1, wherein transmitting the control information to the MBAN terminal includes transmitting the control information in a unicast scheme.

5. The method of claim 1, wherein:
the first frequency band is a band of 2360 MHz to 2390 MHz; and
the second frequency band is a band of 2390 MHz to 2400 MHz.

6. A method of an MBAN (Medical Body Area Network) terminal to initialize an operation channel in an MBAN system, the method comprising:
receiving control information for channel initialization of the MBAN terminal from an MBAN master, wherein the control information includes a channel initializing timer and an action code; and
initializing an operation in a first frequency band when failing to receive a signal through a channel of the first frequency band for a period set by the channel initializing timer; and
starting to search a channel of a second frequency band or another channel of the first frequency band based on the action code and the channel initializing timer,
wherein a value of the channel initializing timer indicates the period from a time when the MBAN terminal cannot receive the signal through the channel of the first frequency band being used to a time when the MBAN terminal starts to search the channel of the second frequency band or another channel of the first frequency band,
wherein the action code indicates a first searching scheme or a second searching scheme,
wherein the first searching scheme is searching the channel of the second frequency band after searching the another channels of the first frequency band,
wherein the second searching scheme is searching the channel of the second frequency band without searching the another channel of the first frequency band,
wherein the first frequency band is a secondary channel for the MBAN terminal,
wherein the second frequency band is a primary channel for the MBAN terminal, and
wherein the period is determined based on a type of a service being used by the MBAN terminal, a history of access of the MBAN terminal to a channel, and an operating scheme of the MBAN master.

7. The method of claim 6, wherein:
the first frequency band is a band of 2360 MHz to 2390 MHz; and
the second frequency band is a band of 2390 MHz to 2400 MHz.

8. An MBAN (Medical Body Area Network) master, comprising:
a controller configured to control channel initialization of an MBAN terminal; and
a wireless communication unit configured to communicate with the MBAN terminal under the control of the controller,
wherein the controller is further configured to:
perform an association process with the MBAN terminal through a channel of a first frequency band, and
control the wireless communication unit to transmit control information for channel initialization of the MBAN terminal to the MBAN terminal,
wherein the control information includes a channel initializing timer,
wherein a value of the channel initializing timer indicates a period from a time when the MBAN terminal cannot receive a signal through a channel of the first frequency band being used to a time when the MBAN terminal starts to search a channel of a second frequency band or another channel of the first frequency band,
wherein the control information further includes an action code,
wherein the action code indicates a first searching scheme or a second searching scheme,
wherein the first searching scheme is searching the channel of the second frequency band after searching the another channel of the first frequency band,
wherein the second searching scheme is searching the channel of the second frequency band without searching the another channel of the first frequency band,
wherein the first frequency band is a secondary channel for the MBAN terminal,
wherein the second frequency band is a primary channel for the MBAN terminal, and
wherein the period is determined based on a type of a service being used by the MBAN terminal, a history of access of the MBAN terminal to a channel, and an operating scheme of the MBAN master.

9. The MBAN master of claim 8, wherein the control information is determined by an MBAN controller.

10. The MBAN master of claim 8, wherein:
the first frequency band is a band of 2360 MHz to 2390 MHz; and
the second frequency band is a band of 2390 MHz to 2400 MHz.

11. An MBAN (Medical Body Area Network) terminal, comprising:
a controller configured to control channel initialization; and
a wireless communication unit configured to communicate with an MBAN master under the control of the controller,
wherein the controller is further configured to:
perform an association process with the MBAN master through a channel of a first frequency band,
receive control information for channel initialization of the MBAN terminal, the control information including a channel initializing timer and an action code, and
when failing to receive a signal through a channel of the first frequency band for a period set by the channel initializing timer, control the wireless communication unit to initialize an operation in the first frequency band and to start to search a channel of a second frequency band or another channel of the first frequency band based on the action code and the channel initializing timer,
wherein a value of the channel initializing timer indicates the period from a time when the MBAN terminal cannot receive the signal through the channel of the first frequency band being used to a time when the MBAN terminal starts to search the channel of the second frequency band or another channel of the first frequency band, wherein the action code indicates a first searching scheme or a second searching scheme, wherein the first searching scheme is searching the channel of the second frequency band after searching the another channel of the first frequency band, wherein the second searching scheme is searching the channel of the second frequency band without searching the another channel of the first frequency band, wherein the first frequency band is a secondary channel for the MBAN terminal, wherein the second frequency band is a primary channel for the MBAN terminal, and wherein the period is determined based on a type of a service being used by the MBAN terminal, a history of access of the MBAN terminal to a channel, and an operating scheme of the MBAN master.

* * * * *